United States Patent [19]

Onishi et al.

[11] Patent Number: 5,540,924
[45] Date of Patent: Jul. 30, 1996

[54] COMPOSITION FOR THE PREVENTION AND TREATMENT OF WHITE DIARRHEA AND DIARRHEA IN LIVESTOCK, ETC.

[75] Inventors: Norimasa Onishi; Akihiro Yamashiro, both of Kawasaki, Japan

[73] Assignee: Ajinomoto Company, Inc., Tokyo, Japan

[21] Appl. No.: 278,868

[22] Filed: Jul. 22, 1994

Related U.S. Application Data

[62] Division of Ser. No. 973,572, Nov. 9, 1992, Pat. No. 5,372,810, which is a continuation of Ser. No. 567,081, Aug. 14, 1990, abandoned.

[30] Foreign Application Priority Data

Sep. 5, 1989 [JP] Japan .................................. 1-229653

[51] Int. Cl.$^6$ .......................... A01N 63/00; A61K 39/05; A61K 39/07; C12N 1/20
[52] U.S. Cl. ................. 424/93.4; 424/246.1; 424/245.1; 435/252.1; 435/252.31; 435/252.32; 435/832; 435/843; 435/853
[58] Field of Search ............... 424/93.4, 520 D, 424/92, 246.1, 245.1; 435/101, 134, 252.1, 252.31, 252.32, 173; 536/7.1, 123

[56] References Cited

U.S. PATENT DOCUMENTS

| | | | |
|---|---|---|---|
| 3,879,545 | 4/1975 | Gaffar et al. | 424/92 |
| 4,094,739 | 6/1978 | Schroeck | 195/7 |
| 4,298,597 | 11/1981 | Acres et al. | 424/92 |
| 4,746,511 | 5/1988 | Kobatake et al. | 424/92 |
| 5,354,671 | 10/1994 | Pollock | 435/101 |

*Primary Examiner*—John W. Rollins
*Assistant Examiner*—Deborah K. Ware
*Attorney, Agent, or Firm*—Oblon, Spivak, McClelland, Maier & Neustadt, P.C.

[57] ABSTRACT

A composition for the prevention and treatment of diarrhea in animals, containing sterilized cells of bacteria belonging to the genus Bacillus, Brevibacterium, Corynebacterium, Escherichia, Lactobacillus, Streptococcus, or Streptomyces, a cell homogenate of said sterilized cells, a cell wall component-containing fraction of said homogenate or mixtures thereof. These ingredients of the composition are admixed into an animal feed.

10 Claims, 4 Drawing Sheets

COMPOSITION FOR THE PREVENTION AND TREATMENT OF WHITE DIARRHEA AND DIARRHEA IN LIVESTOCK, ETC.

This is a division of application Ser. No. 07/973,572, filed Nov. 9, 1992, now U.S. Pat. No. 5,372,810 which was a continuation of 07/567,081, filed Aug. 14, 1990, abandoned.

BACKGROUND OF THE INVENTION

1. Field of the Invention

The present invention relates to novel compositions for the prevention and treatment of white diarrhea or diarrhea in livestock, poultry, pet animals, etc.

2. Discussion of the Background

White diarrhea or diarrhea in suckling pigs during the lactation period is currently one of the most serious problems for swine breeders. About 45 to 70% of swine 2 to 9 weeks of age which are suckling during the lactation and weaning periods suffer from white diarrhea or diarrhea. The economic loss is extremely serious to swine breeders, resulting in a serious problem in the breeding industry. This tendency is also noted in advanced countries. In order to prevent and treat this disease, antibiotics such as sulfa agents or the like are generally used, but in recent years the use of antibiotics has been restricted due to the appearance of resistant bacteria and the internal persistence of the chemicals.

For the prevention and treatment of white diarrhea/diarrhea in livestock or poultry, live bacterial compositions have been developed for use as agents other than antibiotics. In live bacterial compositions, useful live bacteria are directly administered to livestock or poultry, where the bacteria are retained in the intestine of livestock or antagonize enterotoxic bacteria, e.g., *Escherichia coli*, to eliminate the enterotoxic bacteria, during passage of the live bacteria through the intestine. As a result, the enterobacteria microflora is improved so that white diarrhea or diarrhea of livestock is prevented and treated. In order to exhibit this effect, it is necessary that the bacteria be alive. Thus, for purposes of enhancing physicochemical stability of the live bacterial composition in feed and the living animal body, there are reported examples of using spore forming bacteria (cf. Veterinarian and Stockbreeders' News, No. 695, page 343, 1979; Journal of Japanese Veterinary Association. 30, 645 (1977)), and an example of utilizing multi-drug resistant bacteria, taking into account the use in combination with antibiotics as feed additives (Bifidobacteria Microflora, 4, 15 (1985).

However, few live bacterial agents are known to have excellent stability. In addition, the effect is very slow since the mechanism of exhibiting the effect is attributed to elimination of harmful bacteria due to antagonism against the harmful bacteria.

On the other hand, there has been proposed a composition for the prevention and treatment of white diarrhea/diarrhea in livestock or poultry containing as an effective ingredient the enzymatically digested product of cell walls of *Bifidobacterium thermophilum* which is considered to be an intestinal bacteria useful for livestock (cf. Japanese Patent Application Laid-Open No. 56-108717). It is also reported that among cell wall degradation products of bacteria belonging to the genus Bifidobacterium, a peptide glycan is the effective ingredient (cf. Japanese Patent Application Laid-Open No. 62-265231). The mechanism of its activity is quite dissimilar to that of conventional live bacterial agents since the activity is thought to be exhibited due to activation of the immune system of livestock thereby enhancing the ability of livestock to protect itself from infection. These reports are concerned with a method which comprises culturing useful bacteria inherently present in the intestine of livestock, withdrawing the effective component alone and again returning the effective component to the host. The Bifidobacterium used in this method is a strict anaerobe which requires anaerobic operations for incubation of bacterial cells so that the operations become complicated. In addition, expensive raw materials such as vitamins, etc. are required for its growth and cell yield is poor, resulting in high costs.

The agents for the prevention and treatment of white diarrhea/diarrhea by activation of the immune system of livestock are free of the problems of drug resistant bacteria or internal persistence of drugs, unlike antibiotics, and are more highly effective than live bacterial agents. However, such agents are less practical because of difficulty in handling bacteria and the poor yield of bacterial cells.

SUMMARY OF THE INVENTION

Accordingly, one object of the present invention is a composition for the prevention and treatment of white diarrhea/diarrhea in Livestock, poultry, pet animals, etc. which can be readily produced on an industrial scale, can be easily handled and can provide excellent effects by activation of the immune system.

These and other objects which will become apparent from the following specification have been achieved by the present composition which contains at least one of the following: (1) sterilized cells of bacteria belonging to the genus Bacillus, the genus Brevibacterium, the genus Corynebacterium, the genus Escherichia, the genus Lactobacillus, the genus Streptococcus or the genus Streptomyces, (2) a cell homogenate obtained by mechanical homogenization or enzymatic decomposition of the cells of the above named bacteria or (3) a cell wall component-containing fraction obtained by fractionating the above described cell homogenate.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

It has now been discovered that substances containing cell wall components of bacteria belonging to the genus Bacillus, the genus Brevibacterium, the genus Corynebacterium, the genus Escherichia, the genus Lactobacillus, the genus Streptococcus or the genus Streptomyces, which are not intestinal bacteria derived from livestock but which can grow under aerobic conditions, have the effect of preventing and treating white diarrhea or diarrhea of livestock, poultry, pet animals, etc.

That is, the present invention relates to a composition for the prevention and treatment of white diarrhea or diarrhea in livestock, poultry, pet animals, etc. comprising at least one of (1) sterilized cells of bacteria belonging to the genus Bacillus, the genus Brevibacterium, the genus Corynebacterium, the genus Escherichia, the genus Lactobacillus, the genus Streptococcus or the genus Streptomyces, which are not intestinal bacteria derived from livestock but which can grow under aerobic conditions, (2) a cell homogenate obtained by mechanical homogenization or enzymatic decomposition of cells of these bacteria and (3) a cell wall component-containing fraction obtained by fractionating of the cell homogenate.

Examples of the bacteria which can be used in the composition of the present invention for the prevention and treatment of white diarrhea/diarrhea include bacteria belonging to the genus Bacillus such as *Bacillus subtilis* ATCC 13952, etc.; bacteria belonging to the genus Brevibacterium such as *Brevibacterium lactofermentum* ATCC 13869, etc.; bacteria belonging to the genus Corynebacterium such as *Corynebacterium glutamicum* ATCC 13060, etc.; bacteria belonging to the genus Escherichia such as *Escherichia coli* ATCC 8739, etc.; bacteria belonging to the genus Lactobacillus such as *Lactobacillus acidophilus* ATCC 4356, etc.; bacteria belonging to the genus Streptococcus such as *Streptococcus thermophilus* ATCC 19987, etc.; bacteria belonging to the genus Streptomyces such as *Streptomyces tanashiensis* ATCC 15238, etc.

For incubation of these bacteria, any nutrient sources are usable so long as these bacteria can assimilate them. Conventional media may be used, appropriately supplemented with carbohydrates such as glucose, sucrose, etc.; alcohols such as ethanol, glycerol, etc.; organic acids such as acetic acid, propionic acid, etc.; carbon sources such as soybean oil, etc. or a mixture thereof; nitrogen-containing inorganic or organic nutrient sources such as yeast extract, peptone, meat extract, corn steep liquor, ammonium sulfate, ammonia, etc.: inorganic nutrient sources such as phosphates, magnesium, iron, manganese, potassium, etc.; and vitamins such as biotin, thiamine, etc. Incubation may be carried out in a nutrient medium within a pH range of about 4.0 to 9.5 at 20° to 40° C. for 12 hours to 5 days under aerobic conditions.

The cells obtained by the incubation are isolated from the medium and sterilized by a heat treatment, for example. The sterilized cells may be used as they are. However, it is preferred to use homogenized cells. The cells to be homogenized may be either vial cells or sterilized cells. The method of homogenization may be a mechanical method or a method utilizing an enzyme. As an example of the mechanical method, the cells are homogenized using, e.g., a French press, etc. under a pressure of about 800 to 2000 kg/cm$^2$. Alternatively, the cells may also be homogenized with an ultrasonic homogenizer. In the case of homogenizing the bacterial cells using an enzyme, the cultured cells or mechanical homogenate of the cultured cells are suspended in physiological saline, etc. and an enzyme capable of lysing the cell wall is added to the suspension to degrade the cell wall. The enzyme used for this purpose may be any enzyme capable of degrading the cell wall. Representative examples of the enzyme include lysozyme, protease, etc. Known methods and conditions for treatment with the enzyme may be used. In either the mechanical method or the enzyme method, it is preferred that the degree of cell homogenization be about 20%, more preferably about 60%. The degree of homogenization can be determined in terms of the degree of reduction in turbidity of the suspension at a wavelength of 660 nm. In order to increase the degree of homogenization, it is preferred to use the mechanical method and the enzyme method in combination.

The cell homogenate may also be fractionated and the isolated fraction containing cell wall components may be used. Fractionation may be effected by simply centrifuging the cell homogenate to remove insoluble materials. Furthermore, known methods for fractionating proteins, by molecular weight, for example, ultrafiltration, gel filtration, etc. may also be utilized.

The composition of the present invention, that is, the prepared cells, homogenates thereof or fractions containing the cell wall components, may be given orally to livestock, poultry, pet animals, etc. in the form of a liquid, generally an aqueous liquid; or if necessary and desired, the composition may be dried to a powdery form, which is added to feed for livestock, poultry, pets, etc. The composition may be administered at any time, however the effect of the composition for the prevention and treatment of white diarrhea/diarrhea during lactation period is enhanced when the composition is given on consecutive days for 1 to 2 weeks after birth. A daily dose is about 10 mg to about 50 g, preferably about 100 mg to about 2 g, on a dry weight basis. During the weaning period or in poultry, the composition may be added to feed in about 0.01 to 5%, preferably about 0.05 to 1%, on dry weight basis.

In the present invention, livestock includes swine, cow, horse, goat, sheep, etc.; poultry includes fowls such as chicken, etc.; and pets include dogs, cats, etc.

Other features of the invention will become apparent in the course of the following descriptions of exemplary embodiments which are given for illustration of the invention and are not intended to be limiting thereof.

EXAMPLES

Example 1

(1) Preparation of bacterial cells

In a flask of a 500 ml volume was charged 50 ml of medium (pH 7) containing 1.0 g/dl of glucose, 1.0 g/dl of yeast extract, 1.0 g/dl of peptone, 0.5 g/dl of $(NH_4)_2SO_4$, 0.3 g/dl of $K_2HPO_4$, 0.1 g/dl of $KH_2PO_4$ and 0.05 g/dl of $MgSO_4.7H_2O$ followed by sterilization at 115° C. for 15 minutes. *Bacillus subtilis* ATCC 13952, *Brevibacterium lactofermentum* ATCC 13869, *Corynebacterium glutamicum* ATCC 13060, *Escherichia coli* ATCC 8739, *Lactobacillus acidophilus* ATCC 4356, *Streptococcus thermophilus* ATCC 19987 and *Streptomyces tanashiensis* ATCC 15238 were precultured in bouillon agar medium at 30° C. for one day. A loopful of each culture, respectively, was inoculated into separate sterilized medium followed by shake culture at 30° C. for 24 hours. After completion of the culture, each medium was centrifuged to collect the cells. The respective cells were suspended in physiological saline of the same volume as that of the medium followed by a heat treatment at 100° C. for 10 minutes. Each suspension was again centrifuged to collect the cells.

For control, *Bifidobacterium thermophilum* ATCC 25525 (derived from swine intestine) and *Clostridium butylicum* (derived from human intestine) were used as strict anaerobes. In a flask of a 300 ml volume was charged 280 ml of medium (pH 7.0) containing 1.0 g/dl of glucose, 1.0 g/dl of yeast extract, 1.0 g/dl of peptone, 0.02 g/dl of $MgSO_4.7H_2O$, 0.05 g/dl of Tween 80, 0.2 g/dl of ammonium acetate, 10% tomato juice filtrate and 1.0 g/dl of $CaCO_3$ followed by sterilization at 115° C. for 15 minutes. The control bacteria were subjected to stab culture in the same agar medium and then inoculated into the sterilized medium followed by culturing at 37° C. for 2 days under anaerobic conditions. After completion of the culture, each medium was centrifuged to collect the cells. The respective cells were suspended in physiological saline of the same volume as that of the medium. The suspension was heat treated at 100° C. for 10 minutes and again centrifuged to collect the cells.

The weight of the wet cake obtained per 100 ml of medium after the culture is shown in Table 1.

TABLE 1

| | Weight of Wet Cake g/100 ml |
|---|---|
| *Bacillus subtilis* ATCC 13952 | 4.2 |
| *Brevibacterium lactofermentum* ATCC 13869 | 5.6 |
| *Corynebacterium glutamicum* ATCC 13060 | 5.3 |
| *Escherichia coli* ATCC 8739 | 4.5 |
| *Lactobacillus acidophilus* ATCC 4356 | 0.8 |
| *Streptococcus thermophilus* ATCC 19987 | 0.5 |
| *Streptomyces tanashiensis* ATCC 15238 | 2.1 |
| *Bifidobacterium thermophilus* ATCC 25525 | 0.2 |
| *Clostridium butylicum* | 0.3 |

(2) The respective cells (wet cakes) prepared in (1) were suspended in 25 mM phosphate buffer (pH 7.0) at 10 wt %, respectively. The cell suspension was put into a stainless steel bottle (50 ml volume) and treated for 15 minutes at an oscillation frequency of 20 kHz and an output of 200 W using a ultrasonic homogenizer (Model UR-200 P, manufactured by Tomy Seiko Co., Ltd.). After treatment, the homogenate was further centrifuged to obtain a fraction containing the cell wall components.

(3) Enzyme degradation product

To 25 mM phosphate buffer (pH 7.0) containing as a solid content 10 wt % of the mechanical cell homogenate prepared in (2) were added 0.01 wt % of albumen lysozyme (manufactured by Sigma Co.) and 0.02 wt % of actinase (manufactured by Kaken Pharmaceutical Co., Ltd., 7000 units). The mixture was treated at 37° C. for 12 hours and then heat-treated at 100° C. for 2 minutes to inactivate the enzyme.

(4) Effect of immunological activation using mouse spleen cells

Figure 1:
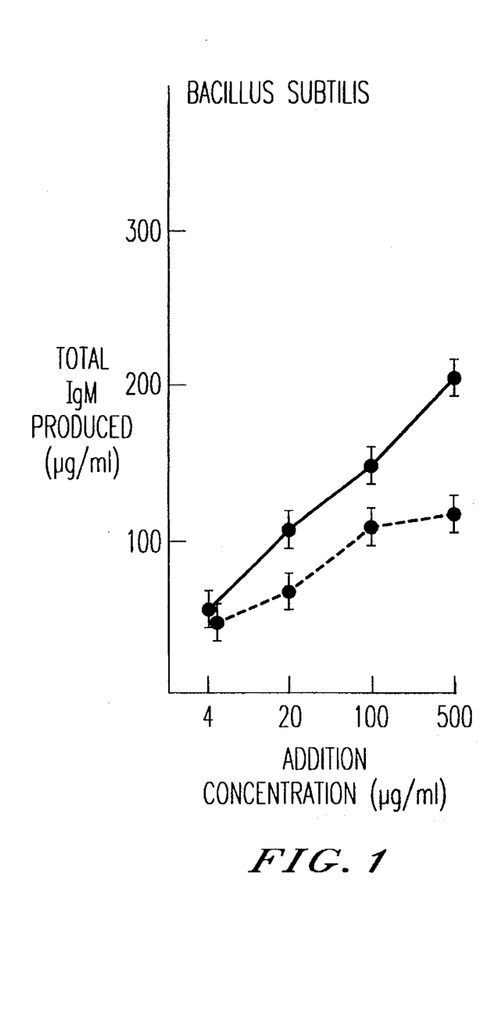
FIG. 1 shows the relationship between the sterilized cells from *Bacillus subtilis* ATCC 13952, its enzyme degradation products and mouse IgM antibody production.
Figure 2:
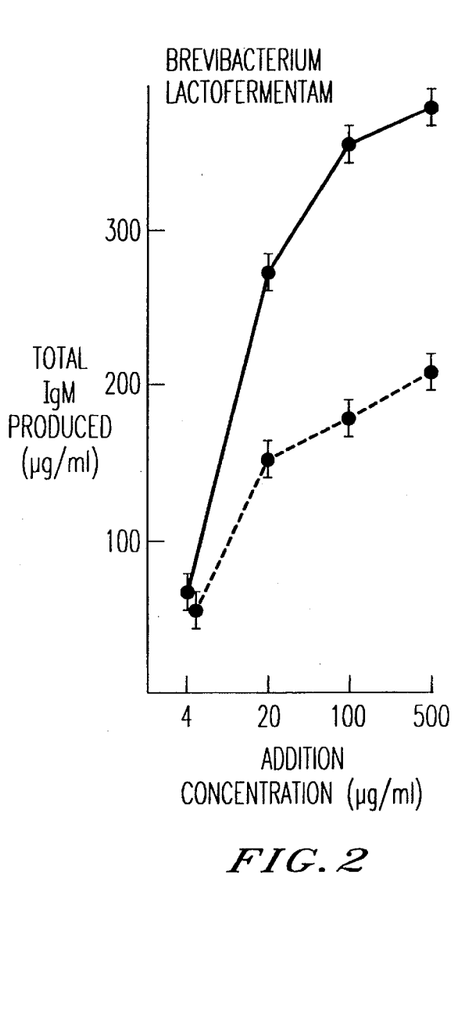
FIG. 2 shows the relationship between the sterilized cells from *Brevibacterium lactofermentum* ATCC 13869, its enzyme degradation products and mouse IgM antibody production.
Figure 3:
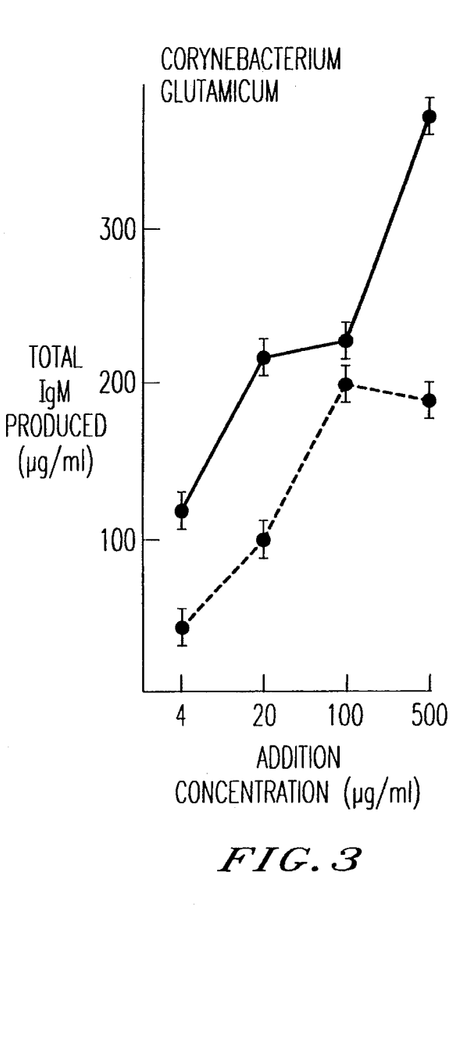
FIG. 3 shows the relationship between the sterilized cells from *Corynebacterium glutamicum* ATCC 13060, its enzyme degradation products and mouse IgM antibody production.
Figure 4:
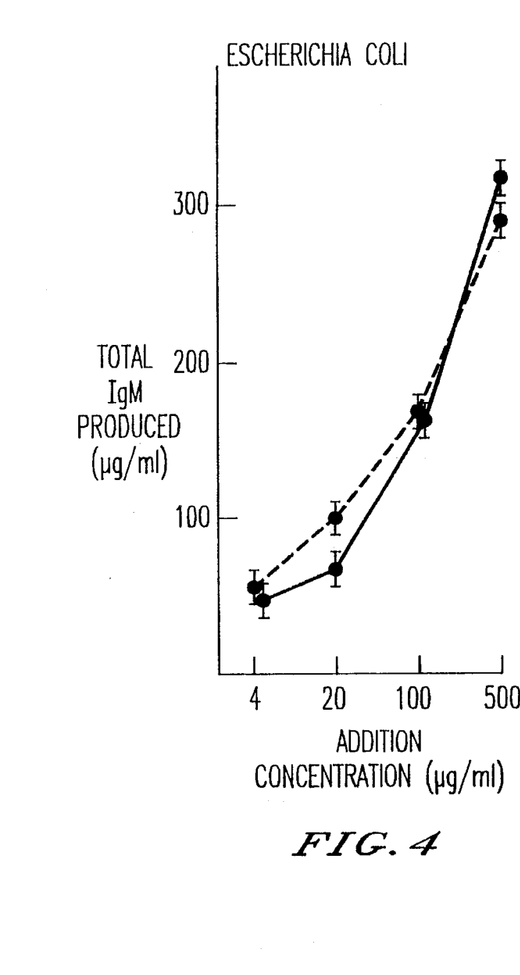
FIG. 4 shows the relationship between the sterilized cells from *Escherichia coli* ATCC 8739, its enzyme degradation products and mouse IgM antibody production.
Figure 5:
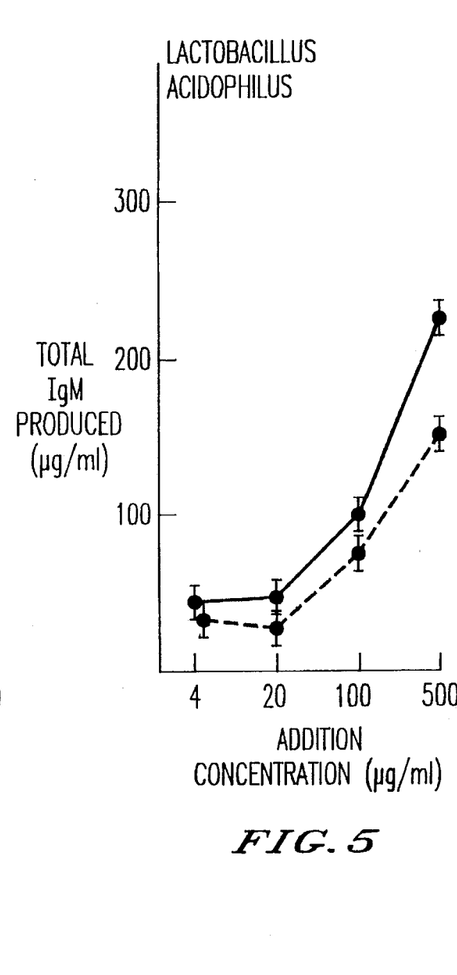
FIG. 5 shows the relationship between the sterilized cells from *Lactobacillus acidophilus* ATCC 4356, its enzyme degradation products and mouse IgM antibody production.
Figure 6:
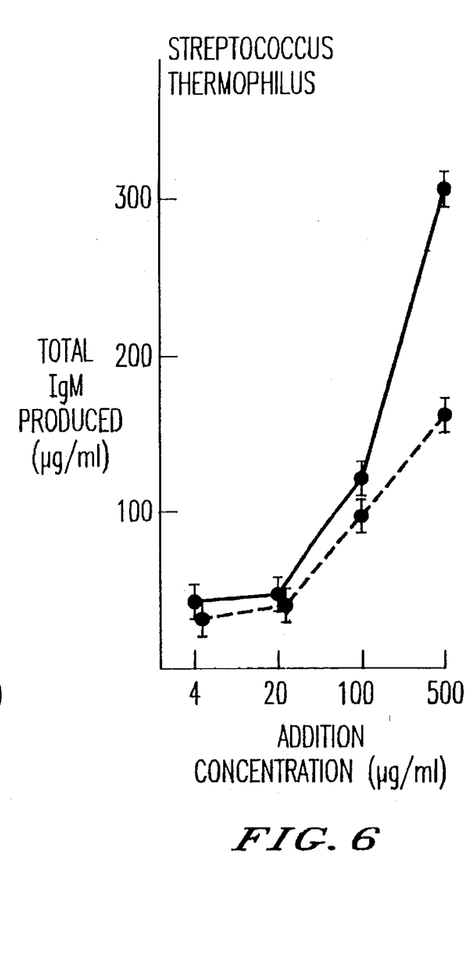
FIG. 6 shows the relationship between the sterilized cells from *Streptococcus thermophilus* ATCC 19987, its enzyme degradation products and mouse IgM antibody production.
Figure 7:
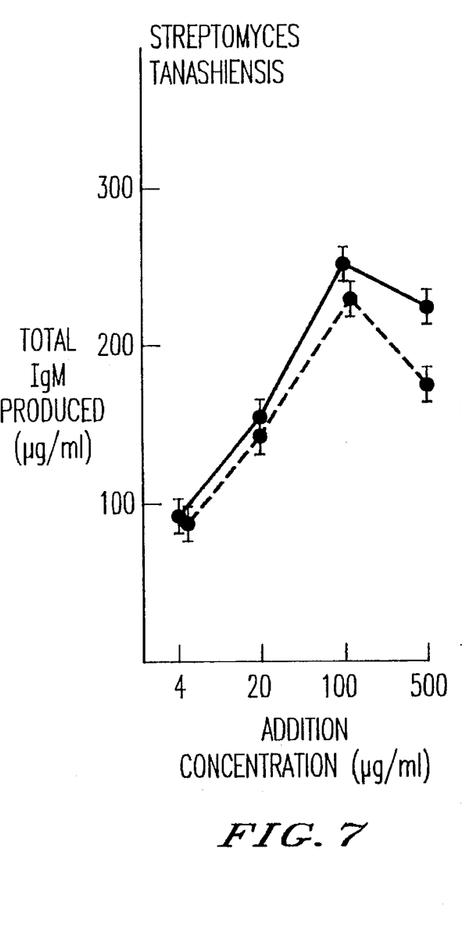
FIG. 7 shows the relationship between the sterilized cells from *Streptomyces tanashiensis* ATCC 15238, its enzyme degradation products and mouse IgM antibody production.
Figure 8:
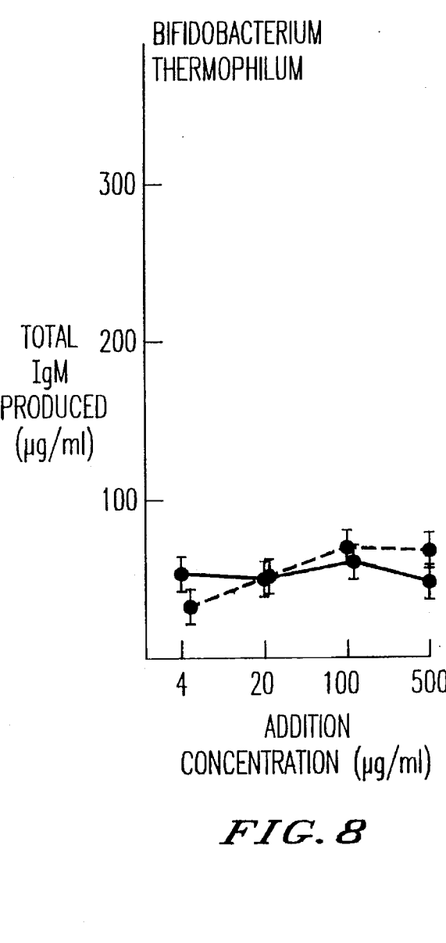
FIG. 8 shows the relationship between the sterilized cells from *Bifidobacterium thermophilum* ATCC 25525, its enzyme degradation products and mouse IgM antibody production, as a control.
Figure 9:
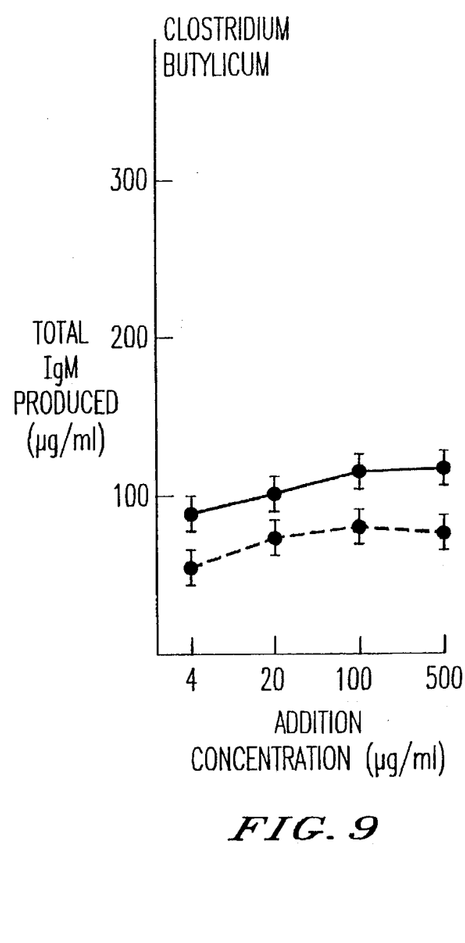
FIG. 9 shows the relationship between the sterilized cells from *Clostridium butylicum*, its enzyme degradation products and mouse IgM antibody production, as a control.
Figure 10:
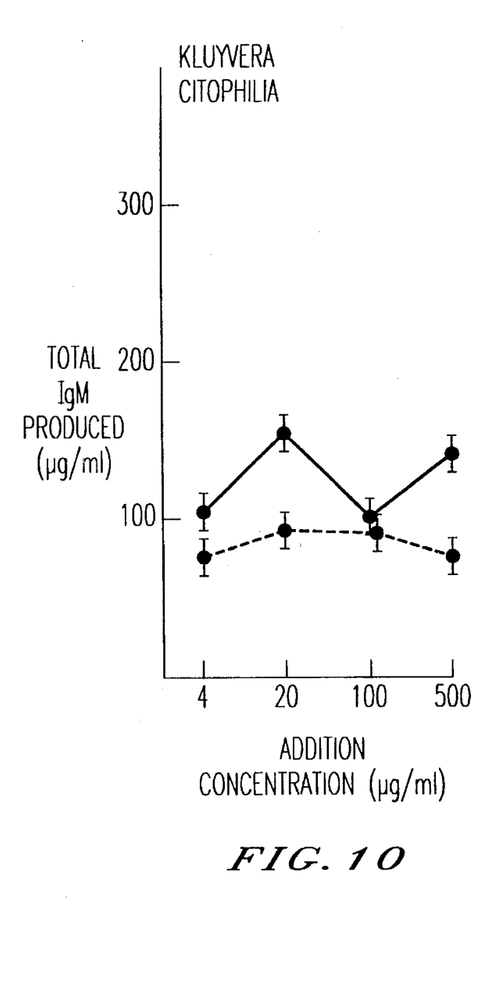
FIG. 10 shows the relationship between the sterilized cells from *Kluyvera citophilia* IFO 8193, its enzyme degradation products and mouse IgM antibody production.
Figure 11:
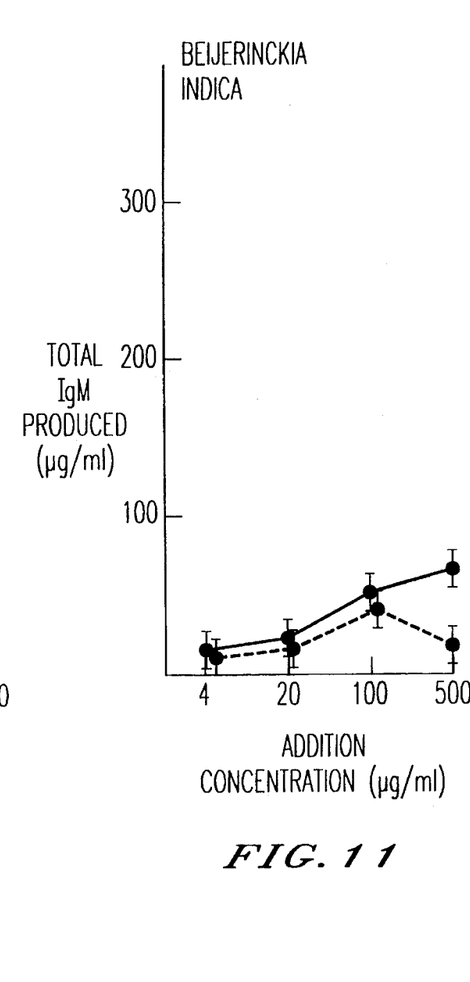
FIG. 11 shows the relationship between the sterilized cells from *Beijerinckia indica* ATCC 9037, its enzyme degradation products and mouse IgM antibody production, as a control.
Figure 12:
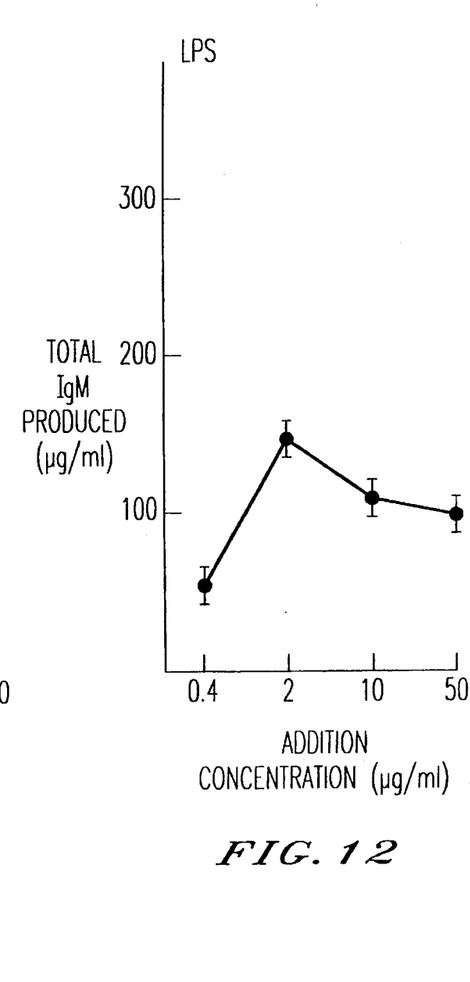
FIG. 12 shows the relationship between sterilized lipopolysaccharide (LPS) derived from pathogenic *Escherichia coli*, its enzyme degradation products and mouse IgM antibody production, as a control.

RPMI 1640 medium was supplemented with 10% immobilized fetal calf serum and $5 \times 10M$ 2-mercaptoethanol, and was then filtered and sterilized. Spleen cells prepared from the spleen of a DBA/2 strain female mouse 10 weeks old were suspended in the sterilized medium at $2.5 \times 10^6$ cells/ml. The cells and enzyme degradation product prepared in (1) and (3), or cells of *Kluyvera citophilia* IFO 8193 or *Beijerinckia indica* ATCC 9037 and the enzyme degradation product prepared in a manner similar to (1) and (3) were added to the suspension, respectively, in the respective concentrations followed by culturing at 37° C. for 4 days in a 5% $CO_2$ incubator. After culturing, the supernatant was diluted 1000-fold with 0.01M Tris-hydrochloride buffer (pH 8.1) containing 1% bovine serum albumin. Thereafter, the total amount of mouse IgM produced in each medium was measured by ELISA to determine the effect of immunological activation of each system. As a standard substance for assaying the effect of immunological activation, lipopolysaccharide (LPS) derived from pathogenic *Escherichia coli* was used. The results are shown in FIGS. 1–12.

FIGS. 1–12 show the relationship between the sterilized cells from each genus, enzyme degradation products thereof and mouse IgM antibody production. In the figure, the abscissa indicates the addition concentration (μg/μl) and the ordinate indicates the concentration (μg/μl) of total mouse IgM produced in the culture broth of spleen culture cells. Broken lines and solid lines show where the sterilized cells were added and where the enzyme degradation products were added, respectively.

As is clear from FIGS. 1–12, the antibody productivity of *Bacillus subtilis* ATCC 13952, *Brevibacterium lactofermentum* ATCC 13869, *Corynebacterium glutamicum* ATCC 13060, *Escherichia coli* ATCC 8739, *Lactobacillus acidophilus* ATCC 4356, *Streptococcus thermophilus* ATCC 19987 and *Streptomyces tanashiensis* ATCC 15238 according to the present invention is higher than that of *Bifidobacterium thermophilum* or *Clostridium butylicum* which are strict anaerobes derived from the intestine of livestock, and higher than that of *Kluyvera citophilia* or *Beikerinckia indica* which are aerobes, in the control groups.

In addition, it can be seen that the antibody productivity of the enzyme degradation products according to the present invention is higher than the antibody productivity of the sterilized cells. The enzyme degradation products all show a high activity exceeding the maximum value (150 g/ml) of the antibody production in LPS, indicating that the enzyme degradation products possess excellent immune activation properties. In contrast, no activity greater than LPS was noted in the control groups. As is also clear from FIGS. 1–12, there is no expectation that antibody production in these control groups could be increased, even if the additive concentration is increased.

(5) Effect on white diarrhea or diarrhea in piglets during lactation

Sixty three (63) piglets during lactation were divided into 9 groups, each group being 7. One group was used as the control (non-administered) group. In the other eight groups, a suspension daily prepared by suspending 200 mg of dry powders of the enzyme degradation products of cells prepared as in (4) in 3 ml of water was orally administered once a day for 7 consecutive days from birth.

For 20 days from Day 8 to Day 27 after birth, the piglets where observed to determine whether white diarrhea or diarrhea had occurred. As shown in Table 2, the incidence of white diarrhea or diarrhea was low and the average body weight increase was high in all of the groups administered the enzyme degradation products of the bacteria of the present invention, as compared to the control group and to the groups administered the enzyme degradation products of *Bifidobacterium thermophilum*.

TABLE 2

| Administered Bacteria | Total Days Observed[1] | Total Days with White Diarrhea or Diarrhea[2] | Body Weight Increase on Day 27 (kg/pig) |
| --- | --- | --- | --- |
| Control (none) | 132[3] | 84 | 4.2 |
| *Bacillus subtilis* ATCC 13952 | 140 | 32 | 6.5 |
| *Brevibacterium lactofermentum* ATCC 13869 | 140 | 25 | 6.8 |
| *Corynebacterium glutamicum* ATCC 13060 | 140 | 28 | 6.5 |
| *Escherichia coli* ATCC 8739 | 140 | 23 | 6.3 |
| *Lactobacillus acidophilus* ATCC 4356 | 140 | 46 | 5.9 |
| *Streptococcus thermophilus* ATCC 19987 | 140 | 36 | 6.1 |
| *Streptomyces tanashiensis* ATCC 15238 | 124[4] | 50 | 5.0 |
| *Bifidobacterium thermophilum* ATCC 25525 | 140 | 58 | 4.8 |

[1]: The number (7) of animals tested × the number (20 days) of days observed = total days observed
[2]: Total days when white diarrhea or diarrhea was observed during the total number of days of observation
[3,4]: One pig each was dead.

(6) Twenty eight (28) piglets during lactation were divided into 4 groups, each group being 7. One group was used as a control (non-administered) group. In the other three groups (administered groups), a suspension daily prepared by suspending 200 mg of dry powders of the heat-treated cells of *Brevibacterium lactofermentum* ATCC 13869 and its mechanical homogenate, also its enzyme degradation products and the fraction thereof prepared as in (1), (2) and (3) in 3 ml of water was orally administered once a day for 7 consecutive days from birth.

For 20 days from Day 8 to Day 27 of the birth, the piglets were observed to determine if white diarrhea or diarrhea had occurred. As shown in Table 3, the incidence of white diarrhea or diarrhea was low and the average body weight increase was high in all of the groups in the present invention, as compared to the control group.

In the administered groups, the effect of preventing white diarrhea or diarrhea was higher in the groups administered with the mechanical homogenate and its enzyme degradation products, than in the group administered with the heat-treated cells.

TABLE 3

| Administered Bacteria | Total Days Observed[1] | Total Days with white Diarrhea or Diarrhea[2] | Body Weight Increase on Day 27 (kg/pig) |
| --- | --- | --- | --- |
| Control (none) | 132[3] | 84 | 4.2 |
| Heat-treated cells | 140 | 46 | 5.4 |
| Mechanical homogenate of cells | 140 | 30 | 6.7 |
| Enzyme degradation products of cells | 140 | 25 | 6.8 |

[1]: The number (7) of animals tested × the number (20 days) of days observed = total days observed
[2]: Total days when white diarrhea or diarrhea was observed during the total number of days of observation
[3]: One pig was dead.

(7) Feeding test of calves by addition to feed

Twelve (12) male calves of the Holstein species, one week old after birth, were divided into 3 groups, one group being a control (non-administered) group. In the other two groups, assorted feed for calves during weaning prepared by adding 0.1 wt. % and 1 wt. % of dry powders of the enzyme degradation products of *Brevibacterium lactofermentum* ATCC 13869 prepared according to (4) was administered (administered groups) and the calves were suckled (lactated) for 3 weeks. During the test period, the incidence of diarrhea and soft feces was observed and the body weight increase was measured.

As shown in Table 4, the incidence of diarrhea and soft feces was low and the body weight increase was good in the administered groups, as compared to the control group. Further in the administered groups, the 1% administered group showed somewhat better results than in the 0.1% administered group.

TABLE 4

| | Incidence of Diarrhea of Soft Feces (%)* | Average Body Weight Increase (kg/calf) |
| --- | --- | --- |
| Control | 82 | 10 |
| 1% Administered Group | 46 | 16 |
| 0.1% Administered Group | 58 | 15 |

$$\text{Incidence of diarrhea or soft feces} = \frac{\text{Number of days when diarrhea or soft feces was observed during the total number of days for observation}}{\text{Total number of days of observation (4 calves} \times \text{21 days)}} \times 100$$

Obviously, numerous modifications and variations of the present invention are possible in light of the above teachings. It is therefore to be understood that within the scope of the appended claims, the invention may be practiced otherwise than as specifically described herein.

What is claimed and desired to be secured by Letters Patent of the United States is:

1. A composition for the prevention and treatment of diarrhea in a domesticated animal, comprising sterilized cells of bacteria belonging to a species selected from the group consisting of *Bacillus subtilis, Brevibacterium lactofermentum, Corynebacterium glutamicum, Escherichia coli, Lactobacillus acidophilus, Streptococcus thermophilus* and *Streptomyces tanashiensis*, a cell homogenate of said sterilized cells, a cell wall fraction of said homogenate or mixtures thereof, admixed into an animal feed.

2. The composition of claim 1, wherein said bacteria species is *Bacillus subtilis*.

3. The composition of claim 1, wherein said bacteria species is *Brevibacterium lactofermentum*.

4. The composition of claim 1, wherein said bacteria species is *Corynebacterium glutamicum*.

5. The composition of claim 1, wherein said bacteria species is *Escherichia coli*.

6. The composition of claim 1, wherein said bacteria species is *Lactobacillus acidophilus*.

7. The composition of claim 1, wherein said bacteria species is *Streptococcus thermophilus*.

8. The composition of claim 1, wherein said bacteria species is *Streptomyces tanashiensis*.

9. The composition of claim 1, wherein said cell homogenate is obtained by a mechanical homogenization or enzymatic homogenization of said sterilized cells.

10. The composition of claim 1, wherein said bacteria is selected from the group consisting of *Bacillus subtilis* ATCC 13952, *Brevibacterium lactofermentum* ATCC 13869, *Corynebacterium glutamicum* ATCC 13060, *Escherichia coli* ATCC 8739, *Lactobacillus acidophilus* ATCC 4356, *Streptococcus thermophilus* ATCC 19987 *and Streptomyces tanashiensis* ATCC 15238.

* * * * *

UNITED STATES PATENT AND TRADEMARK OFFICE
CERTIFICATE OF CORRECTION

PATENT NO. : 5,540,924

DATED : July 30, 1996

INVENTOR(S) : Norimasa ONISHI, et al.

It is certified that error appears in the above-identified patent and that said Letters Patent is hereby corrected as shown below:

Column 1, line 46, "Association.  30,645" should read
   --Association, 30,645--.

Column 6, line 41, "($\mu$g$\mu$l)" should read --($\mu$g/ml)--.
   line 42, "($\mu$g$\mu$l)" should read --($\mu$g/ml)--.
   line 57, "Beikerinckia" should read
   --Beijerinckia--.

Signed and Sealed this

Sixteenth Day of December, 1997

*Attest:*

BRUCE LEHMAN

*Attesting Officer*    Commissioner of Patents and Trademarks